United States Patent
Corsi et al.

(10) Patent No.: US 8,476,446 B2
(45) Date of Patent: *Jul. 2, 2013

(54) ISOXAZOLE DERIVATIVES FOR USE AS FUNGICIDES

(75) Inventors: Camilla Corsi, Stein (CH); Sebastian Volker Wendeborn, Stein (CH); Carla Bobbio, Stein (CH); Jilali Kessabi, Stein (CH); Peter Schneiter, Stein (CH); Valeria Grasso, Stein (CH); Shy-Fuh Lee, Sunnyvale, CA (US); Ulrich Johannes Haas, Stein (CH); Micah Gliedt, Sunnyvale, CA (US)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/133,708

(22) PCT Filed: Dec. 11, 2009

(86) PCT No.: PCT/EP2009/066966
§ 371 (c)(1),
(2), (4) Date: Aug. 26, 2011

(87) PCT Pub. No.: WO2010/069882
PCT Pub. Date: Jun. 24, 2010

(65) Prior Publication Data
US 2011/0301205 A1    Dec. 8, 2011

(30) Foreign Application Priority Data
Dec. 17, 2008    (GB) .................... 0823002.1

(51) Int. Cl.
*C07D 413/00*    (2006.01)
*A01N 43/40*    (2006.01)

(52) U.S. Cl.
USPC ........................ 546/272.1; 514/340

(58) Field of Classification Search
USPC ........................ 546/272.1; 514/340
See application file for complete search history.

(56) References Cited

FOREIGN PATENT DOCUMENTS
WO    2006031631    3/2006
WO    WO 2008/148859    * 12/2008

* cited by examiner

*Primary Examiner* — Janet Andres
*Assistant Examiner* — John Mabry
(74) *Attorney, Agent, or Firm* — R. Kody Jones

(57) ABSTRACT

The present invention relates to isoxazole compounds of formula (I) having fungicidal activity, to agricultural compositions comprising them, and to the use of said compounds and compositions in agriculture for the control of microbial pests, particularly fungal pests, on plants.

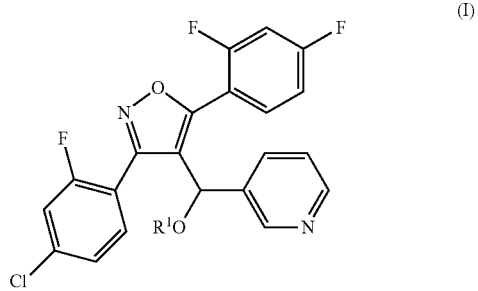

9 Claims, No Drawings

ISOXAZOLE DERIVATIVES FOR USE AS FUNGICIDES

This application is a 371 of International Application No. PCT/EP2009/066966 filed Dec. 11, 2009, which claims priority to GB 0823002.1 filed Dec. 17, 2008, the contents of which are incorporated herein by reference.

The present invention relates to isoxazole compounds having fungicidal activity, to agricultural compositions comprising them, and to the use of said compounds and compositions in agriculture for the control of microbial pests, particularly fungal pests, on plants.

The incidence of serious fungal infections, either systemic or topical, continues to increase for plants, animals, and humans. Many fungi are common in the environment and not harmful to plants or mammals. However, some fungi can produce disease in plants, humans and/or animals.

Fungicides are compounds, of natural or synthetic origin, which act to protect plants against damage caused by fungi, including oomycetes. Current methods of agriculture rely heavily on the use of fungicides. In fact, some crops cannot be grown usefully without the use of fungicides. Using fungicides allows a grower to increase the yield of the crop and consequently, increase the value of the crop. Numerous fungicidal agents have been developed. However, the treatment of fungal infestations and infections continues to be a major problem. Furthermore, fungicide and antifungal drug resistance has become a serious problem, rendering these agents ineffective for some agricultural and therapeutic uses. As such, a need exists for the development of new fungicidal and antifungal compounds (see, e.g., U.S. Pat. No. 6,673,827; See also U.S. Pat. No. 6,617,330 to Walter, which describes pyrimidin-4-enamine as fungicides).

International patent application WO2006/031631 refers to a series of isoxazole derivatives having fungicidal properties. There exists a need therefore for alternative methods of control of fungi. Preferably, new compounds may possess improved fungicidal properties, such as improved efficacy, improved selectivity, lower tendency to generate resistance or activity against a broader spectrum of fungi. Compounds may be more advantageously formulated or provide more efficient delivery and retention at sites of action, or may be more readily biodegradable. Advantageous compounds or their degradation components may generally be less toxic.

It has surprisingly been found that the isoxazole compounds of the present invention exhibit unexpected fungicidal activity and are therefore suitable for use in agriculture as crop protection agents to combat or prevent fungal infestations, or to control other pests such as weeds, insects, or acarids that are harmful to crops.

Accordingly, in a first aspect, the present invention provides a compound of formula (I)

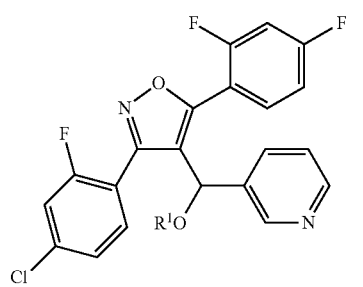

wherein $R^1$ is H or acyl, preferably H;
or an agrochemically acceptable salt thereof.

Acyl includes any readily hydrolysable acyl groups, and comprises, for example, $C(O)R^2$, $C(O)OR^2$, $C(O)NHR^2$ and $C(O)NR^2R^3$, wherein $R^2$ and $R^3$ are each independently selected from alkyl, alkenyl, akynyl, heterocyclyl, aryl and heteroaryl. Acyl groups may be optionally substituted with one or more, for example 1, 2, 3 or 4, halo or $OR^2$ groups. Preferred acyl groups are acetyl, benzoyl and phenylacetyl.

Alkyl groups may be straight, branched or cyclic and contain 1 to 24 carbon atoms. Preferred alkyl groups may contain 1 to 10 carbon atoms, more preferably 1 to 6 carbons, even more preferably 1 to 4 carbon atoms. Representative alkyl groups include, for example, methyl, ethyl, isopropyl, n-propyl, n-butyl, t-butyl, t-amyl, 2,5-dimethylhexyl, cyclobutyl, cyclopropyl, cyclopentyl and cyclohexyl.

Heterocyclyl groups may contain from 3 to 10 ring-atoms up to 4 of which may be hetero-atoms such as nitrogen, oxygen and sulfur, and may be saturated or partially unsaturated. Examples of heterocyclyl groups are oxiranyl, azetidinyl, tetrahydrofuranyl, thiolanyl, pyrrolidinyl, pyrrolinyl, imidazolidinyl, imidazolinyl, sulfolanyl, dioxolanyl, dihydropyranyl, tetrahydropyranyl, piperidinyl, pyrazolinyl, pyrazolidinyl, dioxanyl, morpholinyl, dithianyl, thiomorpholinyl, piperazinyl, azepinyl, oxazepinyl, thiazepinyl, thiazolinyl and diazapanyl.

Aryl includes phenyl, naphthyl, anthracenyl and phenanthrenyl.

Heteroaryl groups may contain from 3 to 10 ring-atoms up to 4 of which may be hetero-atoms such as nitrogen, oxygen and sulfur. Examples of heteroaryl groups are furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyrimidinyl, pyrazinyl, pyridazinyl, tetrazolyl, triazinyl. In addition, the term heteroaryl includes fused heteroaryl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, benzothiazolyl, phthalimido, benzofuranyl, benzodiazepinyl, indolyl and isoindolyl.

Halo means fluoro, chloro, bromo or iodo.

The compounds of the invention include compounds of formula (I) as hereinbefore defined, polymorphs, and isomers thereof, including optical, geometric and tautomeric isomers, and isotopically-labeled compounds of formula (I).

Agrochemically acceptable salts possess a cation, which is known and accepted in the art for the formation of salts for agricultural or horticultural use. Preferably the salts are water-soluble.

Suitable salts of the compounds of formula (I) include acid addition salts such as those with an inorganic acid such as hydrochloric, hydrobromic, sulphuric, nitric or phosphoric acid, or an organic carboxylic acid such as oxalic, tartaric, lactic, butyric, toluic, hexanoic or phthalic acid, or a sulphonic acid such as methane, benzene or toluene sulphonic acid. Other examples of organic carboxylic acids include haloacids such as trifluoroacetic acid.

N-oxides are oxidised forms of tertiary amines or oxidised forms of nitrogen containing heteroaromatic compounds. They are described in many books for example in "Heterocyclic N-oxides" by Angelo Albini and Silvio Pietra, CRC Press, Boca Raton, Fla., 1991.

In a preferred embodiment, the present invention provides a composition comprising a compound of formula (I), or an agrochemically acceptable salt thereof, and an agrochemically acceptable diluent or carrier. References to compounds of the invention herein shall be deemed to include both a compound of formula (I) and agrochemically acceptable salts thereof.

The compound of formula (I) exists as a racemate comprising (R) and (S)-enantiomers. The (S)-enantiomer has been found to have significantly greater fungicidal activity compared to the (R)-enantiomer.

Accordingly, in a preferred aspect, the present invention additionally provides the (S)-enantiomers of the compound of formula (I)

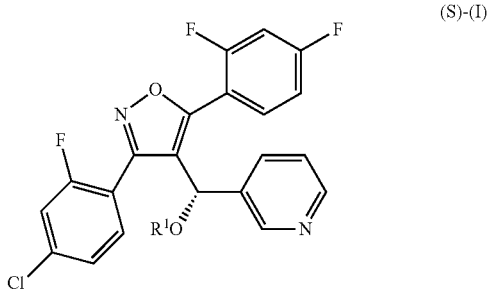

(S)-(I)

wherein $R^1$ is H or acyl, preferably H;
or an agrochemically acceptable salt thereof.

Accordingly, in a preferred aspect, there is provided a composition comprising a compound of formula (S)-(I), or an agrochemically acceptable salt thereof, and an agrochemically acceptable diluent or carrier.

Preferably, the compound of formula (S)-(I) is provided as a single enantiomer having an enantiomeric excess (e.e.) of at least 40%, for example, at least 50%, 60%, 70% or 80%, preferably at least 90%, more preferably at least 95%, yet more preferably at least 98% and most preferably at least 99%.

Most preferably, the compound of formula (I) is (S)-[3-(4-chloro-2-fluorophenyl)-5-(2,4-difluorophenyl)isoxazol-4-yl]pyridin-3-yl-methanol (Example 2)

(S):

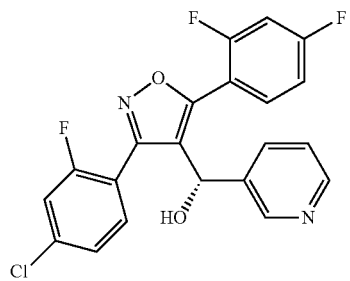

EXAMPLE 2 or an agrochemically acceptable salt thereof.

Preferably, the compound of Example 2 is provided as a single enantiomer having an enantiomeric excess (e.e.) of at least 40%, for example, at least 50%, 60%, 70% or 80%, preferably at least 90%, more preferably at least 95%, yet more preferably at least 98% and most preferably at least 99%.

The compounds and compositions of the present invention are useful for protecting plants against diseases that are caused by fungi, including oomycetes. The compounds of the invention can be used in the agricultural sector and related fields as active ingredients for controlling plant pests. The compounds of the invention can be used to inhibit or destroy the pests that occur on plants or parts of plants (fruit, blossoms, leaves, stems, tubers, roots) of different crops of useful plants, optionally while at the same time protecting also those parts of the plants that grow later e.g. from phytopathogenic micro-organisms.

The compounds and compositions of the present invention may be used as dressing agents for the treatment of plant propagation material, in particular of seeds (fruit, tubers, grains) and plant cuttings (e.g. rice), for the protection against fungal infections as well as against phytopathogenic fungi occurring in the soil.

In an additional aspect, the present invention provides a method of controlling or preventing infestation of cultivated plants by pathogenic microorganisms, comprising applying a compound of formula (I) or composition thereof to said plants, parts thereof or the locus thereof in an amount effective to control said microorganisms.

The compounds and compositions of the present invention may be used against phytopathogenic fungi, for example, those of the following classes: *Fungi imperfecti* (e.g. *Botrytis, Pyricularia, Heiminthosporium, Fusarium, Septoria, Cercospora* and *Alternaria*) and *Basidiomycetes* (e.g. *Rhizoctonia, Hemileia, Puccinia*). Additionally, they may also be used against the *Ascomycetes* classes (e.g. *Venturia* and *Erysiphe, Podosphaera, Monilinia, Uncinula*) and of the *Oomycetes* classes (e.g. *Phytophthora, Pythium, Plasmopara*). Specific examples of *fungi* that may be treated include, but are not limited to, *Septoria tritici, Stagonospora nodorum, Phytophthora infestans, Botrytis cinerea, Sclerotinia homoeocarpa* and *Puccinia recondita*.

In a preferred embodiment of the invention, the compounds and compositions of the present invention are used against the fungal organism *Septoria tritici*.

The crops of useful plants to be protected typically comprise, for example, the following species of plants: cereals (wheat, barley, rye, oats, maize (including field corn, pop corn and sweet corn), rice, sorghum and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, for example, cool-season turf grasses (for example, bluegrasses (*Poa L.*), such as Kentucky bluegrass (*Poa pratensis L.*), rough bluegrass (*Poa trivialis L.*), Canada bluegrass (*Poa compressa L.*) and annual bluegrass (*Poa annua L.*); bentgrasses (*Agrostis L.*), such as creeping bentgrass (*Agrostis palustris Huds.*), colonial bentgrass (*Agrostis tenius Sibth.*), velvet bentgrass (*Agrostis canina L.*) and redtop (*Agrostis alba L.*); *fescues* (*Festuca L.*), such as tall *fescue* (*Festuca arundinacea Schreb.*), meadow *fescue* (*Festuca elatior L.*) and fine *fescues* such as creeping red *fescue* (*Festuca rubra L.*), chewings *fescue* (*Festuca rubra* var. commutate Gaud.), sheep *fescue* (*Festuca ovine L.*) and hard *fescue* (*Festuca longifolia*); and ryegrasses (*Lolium L.*), such as perennial ryegrass (*Lolium perenne L.*) and annual (Italian) ryegrass (*Lolium multiflorum Lam.*)) and warm-season turf grasses (for example, Bermudagrasses (*Cynodon* L. C. Rich), including hybrid and common Bermudagrass; Zoysiagrasses (*Zoysia* Willd.), St. Augustinegrass (*Stenotaphrum secundatum* (Walt.) Kuntze); and centipedegrass (*Eremochloa ophiuroides* (Munro.) Hack.)).

The crops of useful plants also includes plants that have been rendered tolerant to herbicides like bromoxynil or classes of herbicides (such as HPPD inhibitors, ALS inhibitors; for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones (e.g. imazamox) by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The crops of useful plants also includes plants which have been so transformed by the use of recombinant DNA techniques that they are capable of synthesising one or more selectively acting toxins, such as are known from toxin-producing bacteria, especially those of the genus *Bacillus*.

The crops of useful plants also includes plants which have been so transformed by the use of recombinant DNA techniques that they are capable of synthesising antipathogenic substances having a selective action, such as the so-called "pathogenesis-related proteins" (PRPs, see e.g. European patent application EP 0,392,225). Examples of such antipathogenic substances and transgenic plants capable of synthesising such antipathogenic substances are known, for example, from European patent applications EP 0,392,225 and EP 0,353,191, and International patent application WO 95/33818. The methods of producing such transgenic plants are generally known to the person skilled in the art and are described, for example, in the publications mentioned above.

In a preferred embodiment of the invention, the crops of useful plants are selected from cereals, rice, beets, leguminous plants, oil plants, cucumber plants, fibre plants, vegetables, plantation crops, ornamentals, vines, bushberries, caneberries, cranberries, peppermint, rhubarb, spearmint, sugar cane and turf grasses.

The compounds and compositions of the present invention can be applied to the crop area or plant to be treated, simultaneously or in succession with further compounds. These further compounds can be, for example, fertilizers or micronutrient donors or other preparations which influence the growth of plants. They can also be selective herbicides as well as insecticides, fungicides, bactericides, nematicides, molluscicides, plant growth regulators, plant activators or mixtures of several of these preparations, if desired together with further carriers, surfactants or application promoting adjuvants customarily employed in the art of formulation.

The compounds of the present invention can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, pyraclostrobin, picoxystrobin, SSF-129, methyl 2[(2-trifluoromethyl)-pyrid-6-yloxymethyl]-3-methoxy-acrylate or 2-[{.alpha.[(.alpha.-methyl-3-trifluoromethyl-benzyl)imino]oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, harpin, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenylamino-3,5-di-hydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfon-amide (IKF-916), N-(1-cyano-1,2-dimethylpropyl)-2-(2,4-dichlorophenoxy)-propionamide (AC 382042) or iprovalicarb (SZX 722).

The compounds of the present invention can be mixed with one or more systemically acquired resistance inducer ("SAR" inducer), alone or in combination with a fungicide as above. SAR inducers are known and described in, for example, U.S. Pat. No. 6,919,298. In general, a SAR inducer is any compound which has the ability to turn on resistance in a plant to a disease-causing agent, including, but not limited to a virus, a bacterium, a fungus, or combinations of these agents. In addition, an SAR inducer may induce resistance to insect feeding in a plant, as defined by Enyedi et al. (1992; Cell 70: 879-886). Exemplary SAR inducers cover many structural families of compounds, but are united by their ability to induce a resistance to plant diseases and/or pest feeding. One class of SAR inducers is the salicylates. The commercial SAR inducers acibenzolar-s-methyl (available as Actigard® from Syngenta), harpin protein (available as Messenger™ from Eden Biosciences), yeast extract hydrolysate from *Saccharomyces cerevisiae* (available as Keyplex® 350-DP® from Morse Enterprises Limited, Inc. of Miami, Fla.), and Oryzemate are useful in the present invention. Elicitors, including the Goemar products are another class of SAR inducers that can also be used. In addition, ethylene, its biosynthetic precursors, or ethylene releasing compounds such as Ethrel are considered SAR inducers of utility in this context.

Suitable carriers and adjuvants can be solid or liquid and are substances useful in formulation technology, e.g. natural or regenerated mineral substances, solvents, dispersants, wetting agents, tackifiers, thickeners, binders or fertilizers.

A preferred method of application of the compounds and compositions of the present invention is foliar application. The frequency of application and the rate of application will depend on the risk of infestation by the corresponding pathogen. However, the compounds of the present invention can also penetrate the plant through the roots via the soil (systemic action) by drenching the locus of the plant with a liquid formulation, or by applying the compounds in solid form to the soil, e.g. in granular form (soil application). In crops of water such as rice, such granulates can be applied to the flooded rice field. The compounds and compositions of the present invention may also be applied to seeds (coating) by impregnating the seeds or tubers either with a liquid formulation of the fungicide or coating them with a solid formulation.

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, and germinated or soaked seeds.

The term plant propagation material means the generative parts of a plant including seeds of all kinds (fruit, tubers, bulbs, grains etc), roots, rhizomes, cuttings, cut shoots and the like.

Plant propagation material may also include plants and young plants which are to be transplanted after germination or after emergence from the soil.

The compounds of the present invention may be used in unmodified form or, preferably, together with the adjuvants conventionally employed in the art of formulation. To this end they are conveniently formulated in known manner to as granules, wettable or soluble powders, emulsifiable concentrates, coatable pastes, dusts, flowables, directly sprayable or dilutable solutions, suspensions or emulsions, or as controlled release forms such as microcapsules. As with the type of the compositions, the methods of application, such as spraying, atomizing, dusting, scattering, coating or pouring, are chosen in accordance with the intended objectives and the prevailing circumstances.

The compositions of the present invention and, if desired, a solid or liquid adjuvant, are prepared in known manner, typically by intimately mixing and/or grinding the compound with extenders, e.g. solvents, solid carriers and, optionally, surface active compounds (surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners binding agents or fertilizers. Such carriers are for example described in WO 97/33890.

The agrochemical compositions will usually contain from 0.1 to 99% by weight, preferably from 0.1 to 95% by weight, of the compound of formula (I), 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilizers, antifoams, viscosity regulators, binders or tackifiers as well as fertilizers, micronutrient donors or other formulations for obtaining special effects.

Suitably, the agrochemical compositions of the present invention are applied prior to disease development. Rates and frequency of use of the formulations are those conventionally used in the art and will depend on the risk of infestation by the fungal pathogen, the developmental stage of the plant and on the location, timing and application method. Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which control of plant pathogenic fungi is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimeter to 1 centimeter and preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compound of formula (I) and used in the methods of the invention and applied simultaneously or sequentially with the compound of formula (I). When applied simultaneously, these further active ingredients may be formulated together with the compound of formula (I) or mixed in, for example, the spray tank. These further biocidally active ingredients may be fungicides, herbicides, insecticides, bactericides, acaricides, nematicides and/or plant growth regulators.

Accordingly, the present invention provides a composition comprising a compound of formula (I) and (i) a fungicide, (ii) a herbicide, (iii) an insecticide, (iv) a bactericide, (v) an acaricide, (vi) a nematicide and/or (vii) a plant growth regulator.

Additionally, the present invention provides for the use of a composition in the methods of the present invention, said composition comprising a compound of formula (I) and (i) a fungicide, (ii) a herbicide, (iii) an insecticide, (iv) a bactericide, (v) an acaricide, (vi) a nematicide and/or (vii) a plant growth regulator.

The compounds and combinations of the present invention may also be used for controlling fungal infection (particularly by mold and mildew) of technical materials, including protecting technical material against attack of fungi and reducing or eradicating fungal infection of technical materials after such infection has occurred. Technical materials include, for example, organic and inorganic materials wood, paper, leather, natural and synthetic fibers, composites thereof such as particle board, plywood, wall-board and the like, woven and non-woven fabrics, construction surfaces and materials, cooling and heating system surfaces and materials, ventilation and air conditioning system surfaces and materials, and the like. The compounds and combinations according to the present invention can be applied to such materials or surfaces in an amount effective to inhibit or prevent disadvantageous effects such as decay, discoloration or mold in like manner as described above. Structures and dwellings constructed using or incorporating technical materials in which such compounds or combinations have been applied are likewise protected against attack by fungi.

Accordingly, in a further aspect, the present invention provides a method of controlling or preventing infestation of technical materials by pathogenic microorganisms, comprising applying a compound of formula (I) or composition thereof said technical materials, parts thereof or the locus thereof in an amount effective to control said microorganisms.

The compounds and combinations of the present invention may also be used in the treatment of fungal infections of human and animal subjects, such as horses, cattle, sheep, dogs, cats) for medical and veterinary purposes. Examples of such infections include Onychomycosis, sporotichosis, hoof rot, jungle rot, *Pseudallescheria boydii, scopulariopsis* or athletes foot, sometimes generally referred to as "white-line" disease, as well as fungal infections in immunocomprised patients such as AIDS patients and transplant patients. Thus, fungal infections may be of skin or of keratinaceous material such as hair, hooves, or nails, as well as systemic infections such as those caused by *Candida* spp., *Cryptococcus neoformans*, and *Aspergillus* spp., such as as in pulmonary aspergillosis and Pneumocystis carinii pneumonia. The compounds and combinations of the present invention may be combined with a pharmaceutically acceptable carrier and administered or applied to such subjects or infections (e.g., topically, parenterally) in an amount effective to treat the infection in accordance with known techniques.

Accordingly, in a further aspect, the present invention provides a method of treating a fungal infection in a subject in need thereof, comprising administering a compound of formula (I) or composition thereof to said subject in an amount effective to treat said fungal infection.

Compounds of formula (I) may be prepared using the methods below.

Isoxazoles in which $R^1 \neq H$ may be prepared from (I) ($R^1 = H$) using standard acylation or carbamoylation conditions. For example, the acetate derivative of (I) ($R^1 = COCH_3$) may be synthesised from the alcohol (I) ($R^1 = H$) by reaction with acetic anhydride and pyridine in ether solvent at room temperature overnight. Acylations may be carried out using either acid anhydrides (e.g. acetic anhydride, propionic anhydride) or acid chlorides (e.g. benzoyl chloride) in the presence of an organic base in an inert solvent (e.g. ether, dichloromethane). Carbamoylations are effected by treating alcohols (I) with a strong base such as sodium hydride followed by a carbamoyl chloride (e.g. N,N-dimethylcarbamoyl chloride) in an inert solvent such as DMF (dimethylformamide).

EXAMPLE 1

[3-(4-Chloro-2-fluorophenyl)-5-(2,4-difluorophenynl)isoxazol-4-yl]pyridin-3-yl-methanol (i) Preparation of 3-(2,4-difluorophenyl)-1-pyridin-3-yl-propynone (3)

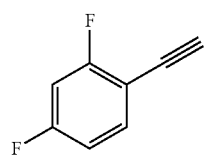

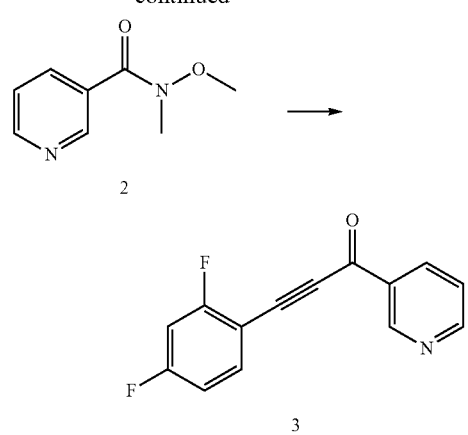

1-Ethynyl-2,4-difluorobenzene (24 g, 0.17 mol) was dissolved in THF (350 ml) and the reaction mixture was cooled at −78° C. A solution of n-BuLi, 2.5 M in hexane, (76.5 ml, 0.19 mol) was added dropwise over 70 minutes maintaining the temperature below −70° C.

The mixture was stirred at this temperature for a further 10 minutes after the addition was finished. A solution of the Weinreb amide 2 (prepared according to WO 05/097760, Letters in Organic Chemistry, 4, 20, 2007) (28.9 g, 0.17 mol) in THF (100 ml) was added dropwise over 20 minutes to the solution above keeping the temperature below −70° C. The mixture was now warmed to −50° C. obtaining a solution that was further stirred for 1 hour at this temperature. The reaction mixture was quenched with a saturated solution of ammonium chloride (100 ml) and allowed to warm to room temperature. The reaction was then poured into a mixture of ethyl acetate/water. Successively, the aqueous phase was washed twice with ethyl acetate. The combined organic layers were washed with brine, dried over sodium sulphate, filtered and concentrated. The crude was recrystallised from diethyl ether obtaining 28 g of the desired product. The mother liquors were concentrated and the residue was purified by column chromatography on alumina using a mixture of cyclohexane/ethyl acetate 3:1. Totally, 29.8 g (70%) of brown compound were obtained.

$^1$H NMR (CDCl$_3$): δ7.02 (m, 1), 7.58 (m, 1), 7.71 (m, 1), 8.56 (m, 1) 8.90 (m, 1) and 9.48 ppm (m, 1). MS m/z: 244.0 (M+H).

(ii) Preparation of [3-(4-chloro-2-fluorophenyl)-5-(2,4-difluorophenyl)isoxazol-4-yl]pyridin-3-yl-methanone (5)

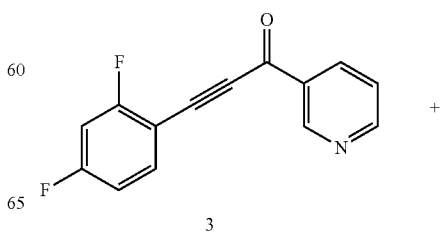

-continued

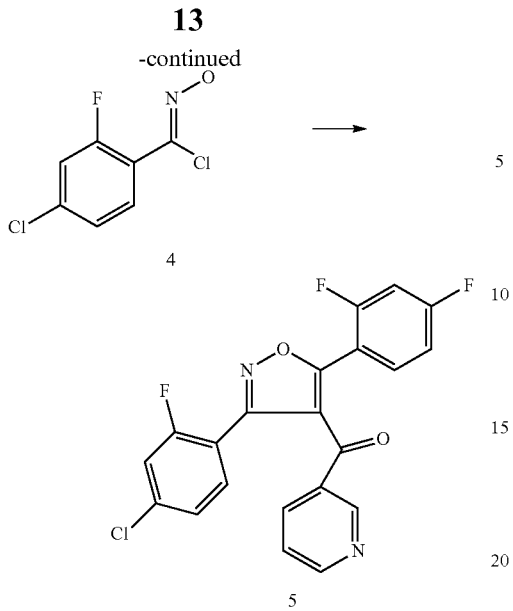

4

5

To a solution of 121 g (697 mmol) of 2-fluoro-4-chloromethylbenzaldehyde oxime in 500 ml of dimethyl formamide was added 93 g (697 mmol) of N-chlorosuccinimide (see K. C. Liu, B. R. Shelton, and R. K. Howe, J. Org. Chem. 1980, 45, 3916). The reaction mixture was stirred at room temperature for two hours and then diluted with ethyl acetate. The ethyl acetate solution was washed with water, saturated sodium chloride and dried over magnesium sulfate. The drying agent was filtered off and solvent removed by rotoevaporation to give 130 g (90%) of yellow crystalline 2-fluoro-4-chloro-N-hydroxybenzenecarboximidoyl chloride.

A mixture of 46.7 g (0.22 mol) of 2-fluoro-4-chloro-N-hydroxybenzenecarboximidoyl chloride, 42 g (0.17 mol) of 3-(2,4-difluorophenyl)-1-pyridin-3-yl-propynone (3), and 21.76 g (0.26 mol) of sodium bicarbonate in 500 mL of isopropyl alcohol was heated at 85° C. for 21 hours. The reaction mixture was diluted with ethyl acetate and washed successively with saturated ammonium chloride, water, and saturate sodium chloride solution, and was dried over magnesium sulfate. The drying agent was filtered off and the ethyl acetate was removed by rotoevaporation. The crude was recrystallised from diethyl ether obtaining the desired product as a yellowish solid (50.28 g, 70.2%).

$^1$H NMR (CDCl$_3$): δ6.75 (m, 1), 7.05 (m, 2), 7.27 (m, 2), 7.67 (t, 1), 7.80 (m, 1), 8.03 (m, 1), 8.66 (m, 1) and 8.82 ppm (d, 1). MS m/z: 415 (M+H).

(iii) Preparation of [3-(4-chloro-2-fluorophenyl)-5-(2,4-difluorophenypisoxazol-4-yl]pyridin-3-yl-methanol (6)

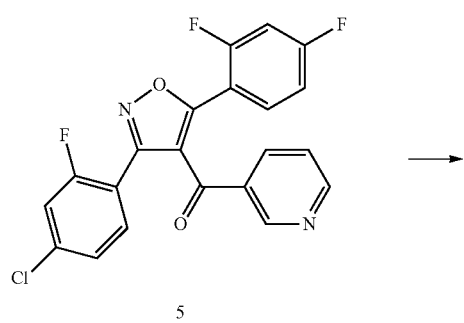

5

-continued

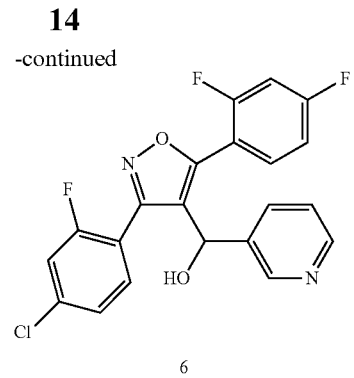

6

To a solution of 5 (26.5 g, 63.9 mmol) in a mixture of THF/methanol (400 ml/40 ml) at 0° C. was added 2.42 g (63.7 mmol) of sodium borohydride. The mixture was stirred for 1.5 hours and then diluted with ethyl acetate. The ethyl acetate solution was washed with saturated sodium chloride solution and dried over magnesium sulfate. The drying agent was filtered off and the ethyl acetate was removed by rotoevaporation. The reaction mixture was purified by column chromatography using a mixture of heptane/ethyl acetate 1:1. The desired compound was obtained as white crystals (17.5 g, 66%). mp=138-140° C.

$^1$H NMR (CDCl$_3$): δ4.19 (bs, 1), 5.89 (s, 1), 6.99 (m, 5), 7.28 (t, 1), 7.43 (d, 1), 7.59 (q, 1), and 8.19 (d, 1) and 8.23 ppm (d, 1). MS m/z: 417 (M+H).

EXAMPLE 2

(S)-[3-(4-chloro-2-fluorophenyl)-5-(2,4-difluorophenypisoxazol-4-yl]pyridin-3-yl-methanol

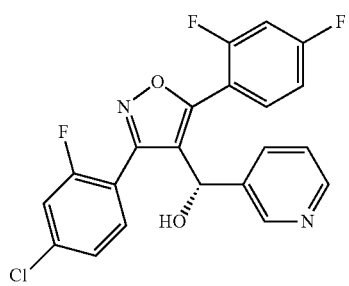 [SMILES: O[C@@H](c1cccnc1)c1c(-c2ccc(Cl)cc2F)noc1-c1ccc(F)cc1F]

Each enantiomer was isolated by preparative chromatography using the racemic mixture 6 as starting material.
Preparative Method:
Column: 250×76 mm CHIRALPAK® AD 20 μm;
Mobil phase: n-heptane/ethanol 70/30 (v/v)
Flow rate: 270 ml/min
Detection: UV 280 nm
Temperature: 25° C.
Analytical Method:
Column: 250×4.6 mm CHIRALPAK® AD-H 5 μm;
Mobil phase: n-heptane/ethanol/diethylamine 70/30/0.1 (v/v/v)
Flow rate: 1 ml/min
Detection: UV 230 nm
Temperature: 25° C.
The first eluting enantiomer had a retention time of 7.6 min ([α]=+58.07, C=0.025 M, THF) while the second enantiomer had a retention time of 9.9 min ([α]=−57.59, C=0.025 M, THF). The second eluting enantiomer is the (S)-enantiomer.

BIOLOGICAL EXAMPLES

The fungicidal properties of Example 2 were demonstrated in the following examples.

*Botrytis cinerea* (Gray mould): Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hours. Example 2 gave at least 80% control of Botrytis cinerea at 200 ppm.

*Mycosphaerella arachidis* (syn. *Cercospora arachidicola*), Brown leaf spot of groundnut (peanut): Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hours at 620 nm. Example 2 gave at least 80% control of *Mycosphaerella arachidis* at 200 ppm.

*Septoria tritici* (leaf blotch): Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hours. Example 2 gave at least 80% control of *Septoria tritici* at 200 ppm.

*Monographella nivalis* (syn. *Microdochium nivale, Fusarium nivale*), snow mould, foot rot of cereals: Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hours at 620 nm. Example 2 gave at least 80% control of *Monographella nivalis* at 200 ppm.

*Fusarium culmorum* (root rot): Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hours. Example 2 gave at least 80% control of *Fusarium culmorum* at 200 ppm.

*Rhizoctonia solani* (foot rot, damping-off): Mycelial fragments of the fungus, prepared from a fresh liquid culture, were directly mixed into nutrient broth (PDB potato dextrose broth). After placing a (DMSO) solution of the test compounds into a microtiter plate (96-well format) the nutrient broth containing the fungal mycelium was added. The test plates were incubated at 24° C. and the inhibition of growth was determined photometrically after 48 h. Example 2 gave at least 80% control of *Rhizoctonia solani* at 200 ppm.

The invention claimed is:

1. A composition comprising:
a compound of the formula (I)

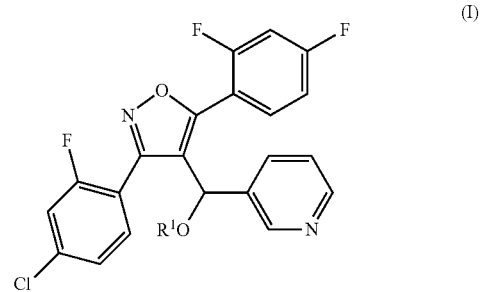

wherein $R^1$ is H or acyl;
or an agrochemically acceptable salt thereof, wherein the compound has an enantiomeric excess of (S) to (R) of at least 80%.

2. A composition according to claim 1 wherein $R^1$ is H.

3. A composition according to claim 1, wherein the compound includes (S)-[3-(4-chloro-2-fluorophenyl)-5-(2,4-difluorophenyl)isoxazol-4-yl]pyridin-3-yl-methanol

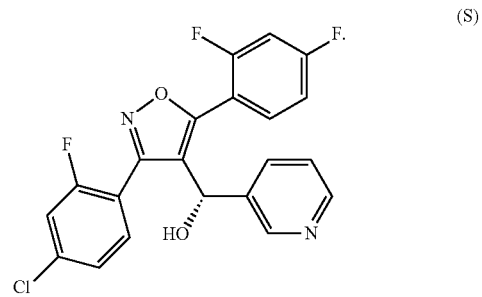 [SMILES: O[C@@H](c1cccnc1)c1c(-c2ccc(Cl)cc2F)noc1-c1ccc(F)cc1F]

4. A composition according to claim 1, further including an agrochemically acceptable diluent or carrier.

5. A composition according to claim 4 further comprising at least one additional fungicide or systemically acquired resistance inducer.

6. A method of controlling or preventing infestation of cultivated plants, plant propagation material, or a technical material, by pathogenic microorganisms, comprising applying a composition according to claim 1, to said plants, parts thereof or the locus thereof, plant propagation material, or technical material in an amount effective to control said microorganisms.

7. A method according to claim 6, wherein said plant propagation material comprises seeds.

8. A method according to claim 7 wherein the pathogenic microorganism is a fungal organism.

9. A method according to claim 8 wherein the fungal organism is selected from *Septoria tritici, Stagonospora nodorum, Phytophthora infestans, Botrytis cinerea, Sclerotinia homoeocarpa* and *Puccinia recondite*.

* * * * *